United States Patent [19]

Yonek et al.

[11] Patent Number: 5,561,211
[45] Date of Patent: *Oct. 1, 1996

[54] BLOCKED POLYISOCYANATES WITH IMPROVED THERMAL STABILITY

[75] Inventors: Kenneth P. Yonek, McMurray; Lyuba K. Gindin, Pittsburgh; Douglas A. Wicks, Mt. Lebanon, all of Pa.

[73] Assignee: Bayer Corporation, Pittsburgh, Pa.

[*] Notice: The term of this patent shall not extend beyond the expiration date of Pat. No. 5,506,327

[21] Appl. No.: 449,403

[22] Filed: May 23, 1995

[51] Int. Cl.$^6$ .............. C08G 18/80; C07C 229/24; C07C 275/16; C07C 275/42
[52] U.S. Cl. ............... 528/45; 528/68; 528/75; 528/84; 560/34; 560/125; 560/155; 564/32
[58] Field of Search .................. 528/45, 68, 75, 528/84; 560/34, 125, 155; 564/32

[56] References Cited

U.S. PATENT DOCUMENTS

| | | | |
|---|---|---|---|
| 3,549,599 | 12/1970 | Merten | 528/73 |
| 3,639,418 | 2/1972 | Merten | 548/314.1 |
| 4,702,953 | 10/1987 | Jonas et al. | 428/209 |
| 5,126,170 | 6/1992 | Zwiener et al. | 427/385.5 |
| 5,236,741 | 8/1993 | Zwiener et al. | 427/385.5 |
| 5,243,012 | 9/1993 | Wicks et al. | 528/58 |
| 5,412,056 | 5/1995 | Zwiener et al. | 528/73 |
| 5,461,135 | 10/1995 | Malofsky et al. | 528/60 |
| 5,506,327 | 4/1996 | Yonek et al. | 528/45 |

FOREIGN PATENT DOCUMENTS 0133519  2/1985  European Pat. Off. .

Primary Examiner—James J. Seidleck
Assistant Examiner—Rabon Sergent
Attorney, Agent, or Firm—Joseph C. Gil; Thomas W. Roy

[57] ABSTRACT

The present invention relates to blocked polyisocyanates containing at least two isocyanate groups which are reversibly blocked with a monofunctional blocking agent for isocyanate groups and at least two isocyanate groups in the form of urea groups, which may be subsequently converted to thermally stable hydantoin groups. The present invention also relates to one-component coating compositions containing these blocked polyisocyanates and compounds containing at least two isocyanate-reactive groups.

9 Claims, No Drawings

BLOCKED POLYISOCYANATES WITH IMPROVED THERMAL STABILITY

BACKGROUND OF THE INVENTION

1. Field of the Invention

The present invention relates to blocked polyisocyanates containing at least two reversibly blocked isocyanate groups and at least two isocyanate groups in the form of urea groups, which may be converted to thermally stable hydantoin groups at elevated temperatures, and to their use in combination with compounds containing isocyanate-reactive groups, especially in electrodeposition coating applications.

2. Description of the Prior Art

Coating compositions containing blocked polyisocyanates are commonly used in the coating industry for the production of one-component coating compositions. Because the isocyanate groups are blocked, they are not reactive under ambient conditions with the isocyanate-reactive component present in the coating composition. However, when the composition is heated to elevated temperatures the blocking agent is released to reform isocyanate groups, which then react with the isocyanate-reactive component to form a coating.

In certain blocked polyisocyanates used in the coatings industry both of the isocyanate groups of the starting polyisocyanate are not reacted with blocking agents. For example, in blocked NCO prepolymers the diisocyanate in the terminal position has one blocked isocyanate group and one isocyanate group which is reacted with, e.g., a polyol.

One of the disadvantages of these compositions is that during the final cure at elevated temperatures the isocyanate group attached to the polymer unblocks (i.e., converts to an isocyanate group and, e.g, a hydroxyl group) at approximately the same temperature as the blocked isocyanate group becomes unblocked. When both sides become detached (unblocked), the diisocyanate monomer tends to migrate to the surface, where it can cause discoloration, e.g, of subsequently applied coating layers.

It is object of the present invention to overcome this problem by providing blocked polyisocyanates in which it is possible to unblock the blocked isocyanate group without unblocking any isocyanate groups which are not intended to be unblocked.

This object may be achieved with the blocked polyisocyanates according to the present invention described hereinafter.

SUMMARY OF THE INVENTION

The present invention relates to blocked polyisocyanates containing at least two isocyanate groups which are reversibly blocked with a monofunctional blocking agent for isocyanate groups and at least two isocyanate groups in the form of urea groups, which may be subsequently converted to thermally stable hydantoin groups, wherein the blocked polyisocyanates correspond to the formula

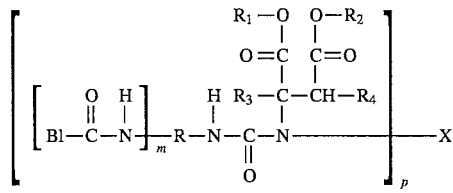

wherein

X represents an organic group which has a valency of p, is inert towards isocyanate groups at a temperature of 100° C. or less and is obtained by removing the aspartate groups from a polyaspartate or an aspartate-functional prepolymer, R represents the residue obtained by removing the isocyanate groups from a polyisocyanate having a functionality of m+1, $R_1$ and $R_2$ may be the same or different and represent optionally substituted hydrocarbon radicals, $R_3$ and $R_4$ may be identical or different and represent hydrogen or organic groups which are inert towards isocyanate groups at a temperature of 100° C. or less, BI represents the residue of a reversible, monofunctional blocking agent for isocyanate groups, m has a value of 1 to 5 and p has a value of 2 to 4.

The present invention also relates to a one-component coating composition containing this blocked polyisocyanate and a compound containing at least two isocyanate-reactive groups.

DETAILED DESCRIPTION OF THE INVENTION

Examples of suitable polyisocyanate starting materials which may be used to prepare the blocked polyisocyanates according to the present invention include monomeric diisocyanates and polyisocyanate adducts, preferably monomeric diisocyanates and more preferably monomeric diisocyanates in which the isocyanate groups do not have the same reactivity with isocyanate-reactive groups.

Suitable monomeric diisocyanates may be represented by the formula $$R(NCO)_2$$

in which R represents an organic group obtained by removing the isocyanate groups from an organic diisocyanate having a molecular weight of about 112 to 1,000, preferably about 140 to 400. Diisocyanates preferred for the process according to the invention are those represented by the above formula in which R represents a divalent aliphatic hydrocarbon group having 4 to 18 carbon atoms, a divalent cycloaliphatic hydrocarbon group having 5 to 15 carbon atoms, a divalent araliphatic hydrocarbon group having 7 to 15 carbon atoms or a divalent aromatic hydrocarbon group having 6 to 15 carbon atoms, Examples of the suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)-methane, 2,4'-dicyclohexyl-methane diisocyanate, 1,3- and 1,4-bis-(isocyanatomethyl)-cyclohexane, bis-(4-isocyanato-3-methyl-cyclohexyl)-methane, α,α,α',α'-tetramethyl-1,3- and/or -1,4-xylylene diisocyanate, 1-isocyanato-1-methyl-4(3)-isocyanatomethyl cyclohexane, 2,4- and/or 2,6-hexahydrotoluylene diisocyanate, 1,3- and/or 1,4-phenylene diisocyanate, 2,4- and/or 2,6-toluylene diisocyanate, 2,4- and/or 4,4'-diphenyl-methane diisocyanate, 1,5-diisocyanato naphthalene and mixtures thereof.

Polyisocyanates containing 3 or more isocyanate groups such as 4-isocyanantomethyl- 1,8-octamethylene diisocyanate and aromatic polyisocyanates such as 4,4',4"-triphenylmethane triisocyanate and polyphenyl polymethylene polyisocyanates obtained by phosgenating aniline/formaldehyde condensates may also be used.

Preferred organic diisocyanates are those from the preceding list in which the isocyanate groups do not have the same reactivity with isocyanate-reactive groups, especially 1-isocyanato-3-isocyanatomethyl- 3,5,5-trimethyl-cyclohexane (isophorone diisocyanate or IPDI), 1,3-bis(isocyanatomethyl)-cyclohexane, 1-isocyanato-1-methyl-4(3)-isocyanatomethyl cyclohexane, 2,4-hexahydrotoluylene diisocyanate, 2,4-toluylene diisocyanate and 2,4-diphenylmethane diisocyanate. Most preferred is 2,4-toluylene diisocyanate.

In accordance with the present invention the polyisocyanate component may also be in the form of a polyisocyanate adduct. Suitable polyisocyanate adducts are those containing isocyanurate, uretdione, biuret, urethane, allophanate, carbodiimide and/or oxadiazinetrione groups. The polyisocyanates adducts have an average functionality of 2 to 6 and an NCO content of 5 to 30% by weight.

1) Isocyanurate group-containing polyisocyanates which may be prepared as set forth in DE-PS 2,616,416, EP-OS 3,765, EP-OS 10,589, EP-OS 47,452, U.S. Pat. No. 4,288,586 and U.S. Pat. No. 4,324,879. The isocyanato-isocyanurates generally have an average NCO functionality of 3 to 3.5 and an NCO content of 5 to 30%, preferably 10 to 25% and most preferably 15 to 25% by weight.

2) Uretdione diisocyanates which may be prepared by oligomerizing a portion of the isocyanate groups of a diisocyanate in the presence of a suitable catalyst, e.g., a trialkyl phosphine catalyst, and which may be used in admixture with other aliphatic and/or cycloaliphatic polyisocyanates, particularly the isocyanurate group-containing polyisocyanates set forth under (1) above.

3) Biuret group-containing polyisocyanates which may be prepared according to the processes disclosed in U.S. Pat. Nos. 3,124,605; 3,358,010; 3,644,490; 3,862,973; 3,906,126; 3,903,127; 4,051,165; 4,147,714; or 4,220,749 by using co-reactants such as water, tertiary alcohols, primary and secondary monoamines, and primary and/or secondary diamines. These polyisocyanates preferably have an NCO content of 18 to 22% by weight and an average NCO functionality of 3 to 3.5.

4) Urethane group-containing polyisocyanates which may be prepared in accordance with the process disclosed in U.S. Pat. No. 3,183,112 by reacting excess quantities of polyisocyanates, preferably diisocyanates, with low molecular weight glycols and polyols having molecular weights of less than 400, such as trimethylol propane, glycerine, 1,2-dihydroxy propane and mixtures thereof. The urethane group-containing polyisocyanates have a most preferred NCO content of 12 to 20% by weight and an (average) NCO functionality of 2.5 to 3.

5) Allophanate group-containing polyisocyanates which may be prepared according to the processes disclosed in U.S. Pat. Nos. 3,769,318, 4,160,080 and 4,177,342. The allophanate group-containing polyisocyanates have a most preferred NCO content of 12 to 21% by weight and an (average) NCO functionality of 2 to 4.5.

6) Isocyanurate and allophanate group-containing polyisocyanates which may be prepared in accordance with the processes set forth in U.S. Pat. Nos. 5,124,427, 5,208,334 and 5,235,018, the disclosures of which are herein incorporated by reference, preferably polyisocyanates containing these groups in a ratio of monoisocyanurate groups to monoallophanate groups of about 10:1 to 1:10, preferably about 5:1 to 1:7.

7) Carbodiimide group-containing polyisocyanates which may be prepared by oligomerizing di- or polyisocyanates in the presence of known carbodiimidization catalysts as described in DE-PS 1,092,007, U.S. Pat. No. 3,152,162 and DE-OS 2,504,400, 2,537,685 and 2,552,350.

8) Polyisocyanates containing oxadiazinetrione groups and containing the reaction product of two moles of a diisocyanate and one mole of carbon dioxide.

Preferred polyisocyanate adducts are the polyisocyanates containing isocyanurate groups, biuret groups and mixtures of isocyanurate groups with either allophanate or uretdione groups. However, the use of polyisocyanate adducts are less preferred according to the invention since the isocyanate groups of these adducts generally have the same reactivity.

The functionality of the polyisocyanates, which corresponds to "m+1" in formula I, is 2 to 6, preferably 2 to 4 and more preferably 2.

To prepare the blocked polyisocyanates according to the invention the isocyanate groups of the starting polyisocyanate are reacted with a reversible, monofunctional blocking agent for isocyanate groups and aspartate group from a polyaspartate or an aspartate-functional prepolymer. The blocking reaction is carried out in known manner by reacting the isocyanate groups with suitable blocking agents, preferably at an elevated temperature (e.g., about 40° to 160° C.), and optionally in the presence of a suitable catalyst, such as a tertiary amine or metal salt.

Suitable blocking agents include monophenols such as phenol, the cresols, the trimethylphenols and the tert. butyl phenols; primary, secondary or tertiary alcohols such as methanol, ethanol, n-propanol, isopropanol, n-butanol, isobutanol, the isomeric pentanols, hexanols and octanols (including branched alcohols such as 2-ethyl hexanol), tert. butanol, tert. amyl alcohol, butyl carbitol, dimethylphenyl carbinol and glycol ethers such as propylene glycol monomethyl ether; compounds which easily form enols such as acetoacetic ester, acetyl acetone and malonic acid derivatives, e.g. malonic acid diethylester; secondary aromatic amines such as N-methyl aniline, the N-methyl toluidine, N-phenyl toluidine and N-phenyl xylidine; imides such as succinimide; lactams such as ε-caprolactam and δ-valerolactam; oximes such as methyl ethyl ketoxime (butanone oxime), methyl amyl ketoxime and cyclohexanone oxime; mercaptans such as methyl mercaptan, ethyl mercaptan, butyl mercaptan, 2-mercapto-benzthiazole, α-naphthyl mercaptan and dodecyl mercaptan; and triazoles such as 1H-1, 2,4-triazole. Preferred blocking agents are the primary monoalcohols such as 2-ethylhexanol and butyl carbitol.

The isocyanate groups that are not blocked are reacted with a polyaspartate containing at least two aspartate groups or an aspartate-functional prepolymer. The polyaspartate corresponds to the formula:

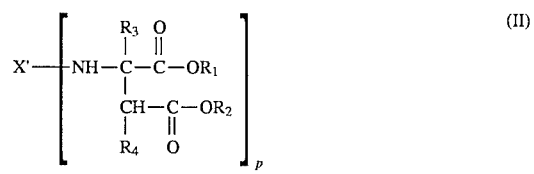

(II)

wherein

X' represents an organic group which has a valency of p, is inert towards isocyanate groups at a temperature of 100° C. or less and is obtained by removing the aspartate groups from a polyaspartate, preferably an organic group having a molecular weight of less than 600 and more preferably an aliphatic, cycloaliphatic, araliphatic or aromatic radical having 2 to 15 carbon atoms, $R_1$ and $R_2$ may be the same or different and represent optionally substituted hydrocarbon radicals, preferably an alkyl radical containing 1 to 9 carbon atoms, more preferably methyl, ethyl or butyl, $R_3$ and $R_4$ may be identical or different and represent hydrogen or organic groups which are inert towards isocyanate groups at a temperature of 100° C. or less, preferably hydrogen and p has a value of 2 to 4, preferably 2 or 3 and more preferably 2.

The polyaspartate may be prepared in known manner by reacting primary amine-containing compounds corresponding to the formula

$$X'—(NH_2)_p \qquad (III)$$

wherein X' and p are as defined above, with optionally substituted maleic or fumaric acid esters corresponding to the formula

$$R_1OOC—CR_3=CR_4—COOR_2 \qquad (IV)$$

wherein $R_1$, $R_2$, $R_3$ and $R_4$ are as defined above.

The polyamines include high molecular weight amines having molecular weights of 800 to about 10,000, preferably 800 to about 6,000, and low molecular weight amines having molecular weights below 800, preferably below 600. The molecular weights are number average molecular weights ($M_n$) and are determined by end group analysis (NH number). Examples of these polyamines are those wherein the amino groups are attached to aliphatic, cycloaliphatic, araliphatic and/or aromatic carbon atoms.

Suitable low molecular polyamines include ethylene diamine, 1,2- and 1,3-propane diamine, 2-methyl-1,2-propane diamine, 2,2-dimethyl- 1,3-propane diamine, 1,3- and 1,4-butane diamine, 1,3- and 1,5-pentane diamine, 2-methyl-1,5-pentane diamine, 1,6-hexane diamine, 2,5-dimethyl- 2,5-hexane diamine, 2,2,4- and/or 2,4,4-trimethyl-1,6-hexane diamine, 1,7-heptane diamine, 1,8-octane diamine, 1,9-nonane diamine, triaminononane, 1,10-decane diamine, 1,11-undecane diamine, 1,12-dodecane diamine, 1-amino-3-aminomethyl-3,5,5-trimethyl cyclohexane, 2,4- and/or 2,6-hexahydrotoluylene diamine, 2,4'- and/or 4,4'-diamino-dicyclohexyl-methane, 3,3'-dialkyl-4,4'-diamino-dicyclohexyl methanes (such as 3,3'-dimethyl-4,4'-diamino-dicyclohexyl methane and 3,3'-diethyl- 4,4'-diaminodicyclohexyl methane), 1,3- and/or 1,4-cyclohexane diamine, 1,3-bis(methylamino)-cyclohexane, 1,8-p-menthane diamine, hydrazine, hydrazides of semicarbazido carboxylic acids, bis-hydrazides, bis-semicarbazides, phenylene diamine, 2,4- and 2,6-toluylene diamine, 2,3- and 3,4-toluylene diamine, 2,4'- and/or 4,4'-diaminodiphenyl methane, higher functional polyphenylene polymethylene polyamines obtained by the aniline/formaldehyde condensation reaction, N,N,N-tris-(2-aminoethyl)-amine, guanidine, melamine, N-(2-aminoethyl)-1,3-propane diamine, 3,3'-diamino-benzidine, polyoxypropylene amines, polyoxyethylene amines, 2,4-bis-(4'-aminobenzyl)-aniline and mixtures thereof. Also suitable are amine-terminated polyethers having the required molecular weight such as the Jeffamine resins, e.g., Jeffamine D-230 and T-403, available from Huntsman.

Suitable high molecular weight polyamines include those prepared from the known polyhydroxyl compounds of polyurethane, especially the polyethers. The polyamines may be prepared by reacting the polyhydroxyl compounds with an excess of the previously described polyisocyanates to form NCO prepolymers and subsequently hydrolyzing the terminal isocyanate group to an amino group. Preferably, the polyamines are prepared by converting the terminal hydroxy groups of the polyhydroxyl compounds to amino groups, e.g., by amination. Preferred high molecular weight polyamines are amine-terminated polyethers such as the Jeffamine resins available from Huntsman.

Preferred polyamines are 1-amino-3-aminomethyl-3,5,5-trimethylcyclohexane (isophorone diamine or IPDA), bis-(4-aminocyclo-hexyl)methane, bis-(4-amino-3-methylcyclohexyl)-methane, 1,6-diamino-hexane, 2-methyl pentamethylene diamine, ethylene diamine, triaminononane, 2,4- and/or 2,6-toluylene diamine, 4,4'- and/or 2,4'-diaminodiphenyl methane and the Jeffamine D-230 and T-403 resins.

Preferred examples of optionally substituted maleic or fumaric acid esters suitable for use in the preparation of the compounds corresponding to formula II include dimethyl, diethyl and di-n-butyl esters of maleic acid and fumaric acid and the corresponding maleic or fumaric acid esters substituted by methyl in the 2- and/or 3-position.

The preparation of the polyaspartates corresponding to formula II from the above mentioned starting materials may be carried out, for example, at a temperature of 0° to 100° C. using the starting materials in such proportions that at least 1, preferably 1, olefinic double bond is present for each primary amino group. Excess starting materials may be removed by distillation after the reaction. The reaction may be carried out solvent-free or in the presence of suitable solvents such as methanol, ethanol, propanol, tetrahydrofuran, dioxane and mixtures of such solvents.

In addition to the definition of X' set forth in the preceding formulas, "X" may also represent the residue obtained by removing the aspartate groups from an aspartate-functional prepolymer containing hydantoin groups or hydantoin group precursors, i.e., urea groups which may converted to hydantoin groups at elevated temperatures. The aspartate-functional prepolymers may be obtained by initially reacting an excess of the previously described polyaspartates, preferably bisaspartates optionally in combination with higher functional aspartates, with monomeric polyisocyanates or polyisocyanate adducts, preferably monomeric diisocyanates, to form aspartate-functional prepolymers containing hydantoin group precursors.

These aspartate-functional prepolymers are prepared by reacting the polyaspartates with the polyisocyanates at a maximum equivalent ratio of aspartate groups (i.e., secondary amino groups) to isocyanate groups of 10:1, preferably 5:1 and more preferably 3:1 and a minimum equivalent ratio of aspartate groups (i.e., secondary amino groups) to isocyanate groups of 1.05:1, preferably 1.5:1 and more preferably 2:1.

The reaction is preferably carried out by incrementally adding the polyisocyanate to the polyaspartate. The reaction to form the urea group-containing intermediate is conducted at a temperature of 10° to 100° C., preferably 20° to 80° C. and more preferably 20° to 50° C. After this addition reaction is complete the resulting aspartate-functional prepolymers contain hydantoin group precursors, i.e., urea groups, and may be used in this form for the preparation of the blocked polyisocyanates according to the invention.

The blocked polyisocyanates according to the invention may be prepared by reacting the polyisocyanate starting material with the monofunctional blocking agent either before, during or after reacting the starting material with the polyaspartate or the aspartate-functional prepolymer. Preferably, the blocking agent is reacted before the aspartate groups under the conditions previously set forth. The blocking agent is used in an amount which is sufficient to block one of the isocyanate groups of a diisocyanate and at least one, but not all of the isocyanate groups of a higher functional polyisocyanate. When a diisocyanate having isocyanate groups with different reactivity is used as the starting material, the amount of blocking agent should most preferably be used in an amount that is sufficient to react with the more reactive isocyanate group.

The remaining isocyanate groups are subsequently reacted with the polyaspartate or aspartate-functional prepolymer to initially form urea groups. The amount of these aspartate groups should be sufficient to react with the remaining isocyanate groups. For example, two moles of a half-blocked diisocyanate containing one unreacted isocyanate group is reacted with one mole of a bis-aspartate, i.e., an NH:NCO equivalent ratio of 1:1. The urea group-forming reaction is carried out at a temperature of 10° to 100° C., preferably 20° to 80° C. and more preferably 20° to 50° C.

It is also possible in accordance with the present invention to react the polyisocyanate with the polyaspartate or aspartate-functional prepolymer prior to blocking a portion of the isocyanate groups with monofunctional blocking agents. In addition, instead of forming the previously described aspartate-functional prepolymers and then reacting them with a partially blocked polyisocyanate to form the blocked polyisocyanates according to the invention, it is also possible to initially prepare an NCO prepolymer and then block the isocyanate groups to form the blocked polyisocyanates according to the invention. The NCO prepolymers are prepared in an analogous manner to the aspartate-functional prepolymers except that an excess of isocyanate groups is used instead of an excess of aspartate groups.

In accordance with a final embodiment of the present invention the residue "X" may also contain blocked isocyanate groups. The blocked isocyanate groups may be introduced during the preparation of the aspartate-functional prepolymer or the NCO prepolymer. For example, instead of using a polyisocyanate to prepare the prepolymers, a compound containing at least two isocyanate groups and at least one blocked polyisocyanate group is used to prepare the prepolymers. In accordance with this embodiment lateral blocking groups are introduced into the product in addition to the terminal blocking groups set forth in formula I).

After the reaction with the blocking agent and the aspartate groups, the blocked polyisocyanates according to the invention are used in their intended application. In accordance with copending application, Attorney's Docket No. MD-93-125B-CT, the blocked polyisocyanates are heated to a temperature of 60° to 240° C., preferably 80° to 160° C. and more preferably 100° to 140° C., to convert the urea groups of the blocked polyisocyanates to the corresponding thermally stable hydantoin groups with elimination of monoalcohols corresponding to the formula R₁OH. However, it is not necessary to convert because convert the urea groups to hydantoin groups prior to using the blocked polyisocyanate in its intended application. This is because during the heating step, which is necessary to unblock the isocyanate groups for subsequent reaction, the urea groups are converted to hydantoin groups in situ.

The invention may be represented by the following reaction scheme using a diisocyanate starting material (in which one of the isocyanate groups is blocked with a blocking agent) and a polyaspartate prepared from a dialkyl maleate and a compound containing two primary amino groups:

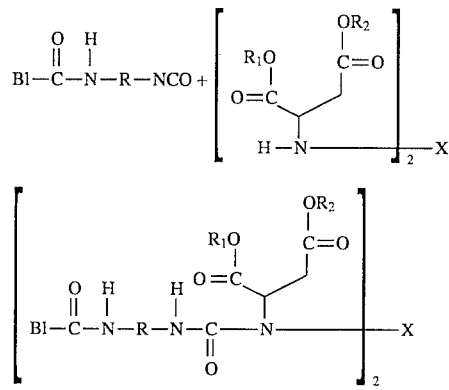

During the subsequent heating step which is necessary to cure the coating compositions according to the invention, the urea groups are converted to hydantoin groups either before or during release of the blocking agent. For purposes of illustration, the following formula sets forth the hydantoin structure obtained from the preceding blocked polyisocyanate assuming that hydantoin formation occurs before the release of the blocking agent:

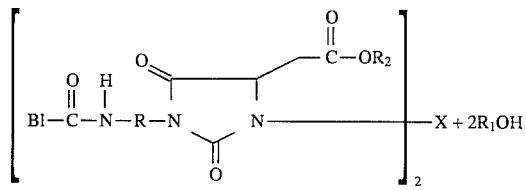

Once formed, the hydantoin groups are thermally stable and do not undergo any chemical change at the temperatures necessary to release the blocking agent.

The blocked polyisocyanates according to the invention are suitable for use in any of the applications where blocked isocyanate groups have previously been used. For example, the blocked polyisocyanates may be blended with other high molecular weight polymers containing at least two isocyanate-reactive groups, preferably the known polyols of polyurethane chemistry, and then cured by heating to an elevated temperature of 100° to 250° C., preferably 120° to 200° C., which is sufficient to release the blocking agent and reform the isocyanate group. The blocked polyisocyanates according to the invention are especially suited for use in electrodeposition coating processes.

To accelerate hardening, the coating compositions may contain known polyurethane catalysts, e.g., tertiary amines such as triethylamine, pyridine, methyl pyridine, benzyl dimethylamine, N,N-dimethylamino cyclohexane, N-methyl-piperidine, pentamethyl diethylene triamine, 1,4-diazabicyclo[2,2,2]-octane and N,N'-dimethyl piperazine; or metal salts such as iron(III)-chloride, zinc chloride, zinc-2-ethyl caproate, tin(II)-ethyl caproate, molybdenum glycolate and dialkyltin(IV) complexes, e.g., dibutyltin(IV)-dilaurate.

The coating compositions may also contain other additives such as pigments, dyes, fillers, levelling agents and solvents. The coating compositions may be applied to the substrate to be coated by conventional methods such as painting, rolling, pouring or spraying.

Coating compositions containing the blocked polyisocyanates according to the invention provide coatings which adhere surprisingly well to a variety of materials including metal substrates and basecoats (especially those used in the automotive industry), and are very resistant to abrasion. Furthermore, they are characterized by high hardness, elasticity, very good resistance to chemicals, high gloss, excellent weather resistance, excellent environmental etch resistance and good pigmenting qualities.

The invention is further illustrated, but is not intended to be limited by the following examples in which all pads and percentages are by weight unless otherwise specified. Isocyanate contents and equivalents weights are based on the weight of the solution unless otherwise specified.

EXAMPLES

Half-blocked isocyanate 1

The reaction product of one mole of 2,4-toluylene diisocyanate with one mole of 2-ethyl hexanol.

Half-blocked isocyanate 2

174.0 pads (1 mole) of 2,4-toluylene diisocyanate and 0.08 pads of benzoyl chloride were charged into a 3-neck flask equipped with a stirrer, thermometer and an addition funnel and mixed for 1 hour at room temperature. Then 162 pads of 2-(2-butoxyethoxy)-ethanol (butyl carbitol) were slowly added dropwise to the diisocyanate. The temperature was maintained below 30° C. during and after the addition. The resulting product had a viscosity of 353 mPa.s at 25° C., an equivalent weight of 337.35 and an isocyanate content of 12.42%.

Bis-aspartate 1

116 pads of 2-methyl-1,5-pentanediamine (1.0 mole) were added dropwise with stirring to 456 pads of maleic acid dibutylester (2.0 moles) that were previously charged at ambient temperature to a 1 L three necked flask equipped with a stirrer, thermometer and an addition funnel. The amine was added at a rate such that the exotherm did not increase the temperature of the reaction mixture above 50° C. Upon complete addition the contents of the reaction flask were maintained at 50° C. for a period of 12 hours. The resulting product was a clear, colorless liquid having a viscosity of about 64 mPa.s (25° C.) and an amine equivalent weight of about 286.

Bis-aspartate 2

516 pads of maleic acid diethylester (3.0 moles) were added dropwise with stirring to 403 parts (1.0 mole) of a trifunctional, amine-terminated, propylene oxide polyether (Jeffamine T-403 available from Huntsman) that were previously charged at ambient temperature to a 2 L three necked flask equipped with a stirrer, thermometer and an addition funnel. The diester was added at a rate such that the exotherm did not increase the temperature of the reaction mixture above 50° C. Upon complete addition the contents of the reaction flask were maintained at 50° C. for a period of 12 hours. The resulting product was a clear, colorless liquid having a viscosity of about 96 mPa.s (25° C.) and an amine equivalent weight of about 306.

Bis-aspartate 3

116 parts of 2-methyl-1,5-pentanediamine (1.0 mole) were added dropwise with stirring to 344 parts of maleic acid diethylester (2.0 moles) that were previously charged at ambient temperature to a 1 L three necked flask equipped with a stirrer, thermometer and an addition funnel. The amine was added at a rate such that the exotherm did not increase the temperature of the reaction mixture above 50° C. Upon complete addition the contents of the reaction flask were maintained at 50° C. for a period of 12 hours. The resulting product was a clear, colorless liquid having a viscosity of about 90 mPa.s (25° C.) and an amine equivalent weight of about 230.

Example 1

Blocked polyisocyanate from half-blocked isocyanate 1 and bis-aspartate 3

85.152 g (0.28 moles) of half-blocked isocyanate 1 were added dropwise to 64.49 g (0.14 moles) of bis-aspartate 3 at 80° C. The reaction was allowed to continue at this temperature until the formation of urea groups was complete, which took approximately 1 hour.

Examples 2–5

Blocked polyisocyanates were prepared following the procedure set forth in Example 1 from the half-blocked isocyanates and bis-aspartates set forth in the following table. The molar ratio of the reactants is set forth in the table. The amine number of the products was 0, indicating that the reaction continued to completion.

| Example | 2 | 3 | 4 | 5 |
|---|---|---|---|---|
| Isocyanate | 1 | 2 | 2 | 1 |
| Amount | 101.09 | 431.15 | 393.27 | 85.51 |
| Bis-aspartate | 1 | 1 | 2 | 3 |
| Amount | 98.91 | 368.85 | 356.73 | 64.49 |
| Molar ratio Isocyanate/aspartate | 2:1 | 2:1 | 3:1 | 2:1 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A blocked polyisocyanate containing at least two isocyanate groups which are reversibly blocked with a monofunctional blocking agent for isocyanate groups and at least two isocyanate groups in the form of urea groups, which can be subsequently converted to thermally stable hydantoin groups, wherein the blocked polyisocyanate corresponds to the formula

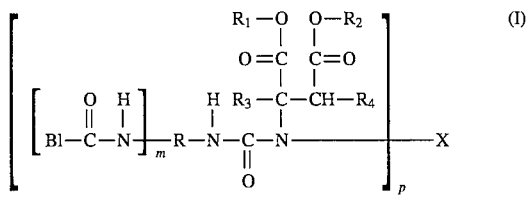

wherein

X represents an organic group which has a valency of p, is inert towards isocyanate groups at a temperature of 100° C. or less and is obtained by removing the aspartate groups from a polyaspartate or an aspartate-functional prepolymer, R represents the residue obtained by removing the isocyanate groups from a polyisocyanate having a functionality of m+1, $R_1$ and $R_2$ are the same or different and represent optionally substituted hydrocarbon radicals, $R_3$ and $R_4$ are the same or different and represent hydrogen or organic groups which are inert towards isocyanate groups at a temperature of 100° C. or less, BI represents the residue of a reversible, monofunctional blocking agent for isocyanate groups, m has a value of 1 to 5 and p has a value of 2 to 4.

2. The blocked polyisocyanate of claim 1 wherein $R_1$ and $R_2$ are the same or different and represent alkyl groups having 1 to 9 carbons, $R_3$ and $R_4$ represent hydrogen and m is 1.

3. The blocked polyisocyanate of claim 1 wherein p is 2 or 3.

4. The blocked polyisocyanate of claim 2, wherein p is 2 or 3.

5. The blocked polyisocyanate of claim 1 wherein R represents the residue obtained by removing the isocyanate groups from a diisocyanate having isocyanate groups of different reactivity.

6. The blocked polyisocyanate of claim 2 wherein R represents the residue obtained by removing the isocyanate groups from a diisocyanate having isocyanate groups of different reactivity.

7. The blocked polyisocyanate of claim 3 wherein R represents the residue obtained by removing the isocyanate groups from a diisocyanate having isocyanate groups of different reactivity.

8. The blocked polyisocyanate of claim 4 wherein R represents the residue obtained by removing the isocyanate groups from a diisocyanate having isocyanate groups of different reactivity.

9. A coating composition containing the blocked polyisocyanate of claim 1 and a compound containing at least two isocyanate-reactive groups.

* * * * *